United States Patent [19]

Vecchi

[11] Patent Number: 5,318,983
[45] Date of Patent: Jun. 7, 1994

[54] TRISUBSTITUTED PYRROLE DERIVATIVES HAVING ANTIFUNGINE ACTIVITY, AND RELATED PHARMACEUTICAL COMPOSITIONS

[75] Inventor: Giuseppe Vecchi, Aldesago, Switzerland

[73] Assignee: APR Applied Pharma Research S.A., Lugano, Switzerland

[21] Appl. No.: 982,700

[22] Filed: Nov. 30, 1992

[30] Foreign Application Priority Data

Nov. 29, 1991 [CH] Switzerland .................. 03510/91

[51] Int. Cl.⁵ .................. A61K 31/415; C07D 403/10
[52] U.S. Cl. .................. 514/397; 548/314.7
[58] Field of Search .................. 548/314.7; 514/397

[56] References Cited
FOREIGN PATENT DOCUMENTS 0015155  2/1980  European Pat. Off. .
0166556  1/1986  European Pat. Off. .

Primary Examiner—Patricia L. Morris
Attorney, Agent, or Firm—Nixon & Vanderhye

[57] ABSTRACT

The pyrrole derivatives having the general formula:

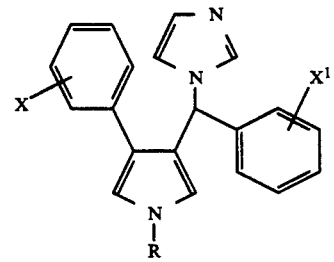

wherein X and X' represent H, alkyl, alkoxy, halogen, nitro, amino, and R is H, alkyl, aryl, arylalkyl, cycloalkylmethyl, are active against pathogenic microorganisms, and particularly against mycetes and Gram-positive and Gram-negative bacteria.

8 Claims, No Drawings

TRISUBSTITUTED PYRROLE DERIVATIVES HAVING ANTIFUNGINE ACTIVITY, AND RELATED PHARMACEUTICAL COMPOSITIONS

The present invention relates to novel pyrrole derivatives having anti-mycotic and anti-bacterial activity.

Mycosis: ethiopathogenetic framing.

The mycoses, both superficially and deeply set in, are pathologies of increasingly greater diffusion, owing to factors either of environmental nature (climate, modifications of the bacterial microflora, etc.), and of individual origin (diabetes, congenital or acquired immunodeficiencies, pharmacological treatments, etc.). Among the cutaneous surface mycoses are worth of attention the following: pityriasis versicolor, induced by the invasion of the corneal layer by the *Pitirosporum orbicularis*; epidermomycosis of the glabrous parts (tinea corporis), induced by the localization in the glabrous cutis of dermatophytes mainly of the genus Microsporum and Epidermophyton; inguinal epidermophytis, i.e. a mycotic intertrigo prevailingly localized at the inguinal and scrotal area induced by a dermatophyte, *Epidermophyton floccosum*; tineae, i.e. normally infantile hair dermatophytosis, characterized by erythema, scaling and hair alterations, supported by fungi of the genera Trichophyton and Microsporum, onychoses induced by *Candida albicans* Trichophyton and other fungi.

In the field of the mycology the *Candida albicans* represents a specific chapter. The Candida induced infections are often superficial; among them it is worth to mention: submammary, inguinocrural, perianal and axillary intertrigines, the interfinger intertrigo of the hands, stomatitis, chititis, vulvovaginitis, barnacle posthitis and perionyxis. Much more important are the muco-cutaneous chronical candidiasis (also involving granulation hyperplasic features) and above all the systemic candidiasis (esophageous, lung and other invasive pathologies, sepsis with visceral embolic diffusion, etc.), forms associated with other pathologies (tumoral etc.) and immunoconditioned.

Lastly, systemic fungine infections or deep mycoses are induced from a number of diseases originated by non keratinophilic mycetes, these infections not always involving the cutis (to which they may arrive by haematogenic route, with an often extracutaneous inlet) and which can have a serious course.

Antifungine therapy: state of the art.

The chemiotherapy of the fungine infections is still nowadays an important therapeutical problem, very far from the ideal solution from the point of view of the effectiveness and of the tolerability. The substances having anti-mycotic activity can be grouped into two categories namely the natural antibiotics and the synthesis products.

A) Antibiotics.

The polyenes (amphotericin B) and the griseofulvin are well known antibiotics of widespread therapeutical use. The group of the polyenic antibiotics includes a relevant number of substances derived from several species of *Streptomyces*. 87 of them are known, mostly unstable or toxic.

The chemical structure of the polyenic antibiotics is a macrolide ring of carbon atoms containing a variable number of conjugated double bonds. These polyenic antibiotics are bound to the ergosterol of the plasma membrane inducing an increase of the permeability thereof: it occurs both by a rearrangement of the lipidic molecules and owing to a fragmentation of the membrane. The inhibiting activity is high for yeasts and dimorphic fungi, whereas the dermatophytes (which are included among the main causes of cutaneous mycoses) and the mycetes belonging to the group of the Dematiaceae are generally resistant. The amphotericin B, moreover, has a toxicity represented by a reduced medullary erythropoiesis, haemolytic anemia, hypotension, renal vasal constriction with cortical ischemia and reduction of the glomerular filtrate.

The griseofulvin chemically is an octahedron of benzene: the action mechanism thereof comprises several phases not yet fully clarified. In vitro the griseofulvin is active against all the dermatophytes at very low concentrations, but in vitro the griseofulvin in fungistatic and not fungicide: the antibiotic destroys the mycelium in the growth phase but not the quiescent hyphae, whereby a complete destruction of the mycosis is prevented.

B) Synthesis chemiotherapeutical agents.

This field of the chemiotherapy is still the object of active and promising research work. The hystorically most important chemiotherapeutical substances are represented from tolnaftate, haloprogin and 5-fluorocytosine. The former two compounds have been for years the only valable drug for the treatment of surface and deep mycoses; they are however affected by toxic and allergenic properties whereby their therapeutical use is actually diminished and other preparates are used in substitution therefor.

The 5-fluorocytosine belongs to the group of the fluorinated pyrimidines; the inhibiting activity takes essentially place on the yeasts and on the Demantiaceae, whereas it is variable against other filamentary fungi and is absent against the dermatophytes and the dimorphic fungi, inducing the dermatomycoses. Thus the 5-fluorocytosine is not suitable for the treatment of the surface mycotic infections. The anti-fungine chemiotherapy has been strongly promoted after 1970 owing to the discovery of azoles having a wide anti-fungine spectrum. Among the imidazole derivatives, miconazole, econazole, ketoconazole, chlotrimazole and thioconazole, and among the triazole derivatives, fluconazole and flutriazole, are the mostly used compounds in the treatment of cutaneous and systemic mycoses. However also the use of these compounds can lead to a therapeutical failure, if the action spectrum of the compound is too much limited, if the antifungine activity is slowly developed thus permitting resistant strain to be generated, or if the treatment is affected by toxicity phenomena.

The pharmacological research work is thus still active in the development of molecules having a wider action spectrum, broadened to the Gram+ and Gram- bacteria too, often responsible of combined mycotic-bacterial infections, as well as molecules having remarkable and fast mycocide action permitting shorter and more resolving therapies.

The main purpose of the present invention is that of providing novel compounds having the above indicated characteristics and properties.

This purpose is achieved with the compounds of the present invention consisting in pyrrole derivatives having general formula:

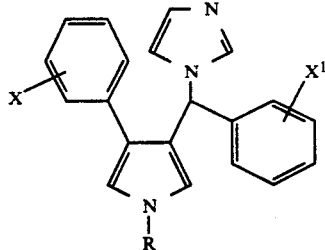

FIG. 1 wherein X and X' represent H, alkyl, alkoxy, halogen, nitro, amino and R represents H, alkyl, aryl, arylalkyl, cycloalkylmethyl.

Some of the compounds of the present invention have been the subject of specific preparations and their main physical and chemical characteristics are reported in the Tables 1 and 2.

TABLE 1

3-ARYL-4(α-(1 H-IMIDAZOL-1-YL) BENZYL-1H-PYRROLES-1-SUBSTITUTED

| Abbreviation | X | R | X' |
|---|---|---|---|
| RDA 106 | H | H | H |
| RDA 124 | H | CH3 | H |
| RDS 120 | H | A | H |
| RDS 126 | Cl | H | H |
| RDS 125 | Cl | CH3 | H |
| RDS 133 | Cl | A | H |
| RDS 128 | F | H | H |
| RDS 134 | F | CH3 | H |
| RDS 132 | F | A | H |
| RDS 138 | OCH3 | H | H |
| RDS 139 | OCH3 | CH3 | H |
| RDS 141 | OCH3 | A | H |
| RDS 143 | CH3 | H | H |
| RDS 168 | CH3 | CH3 | H |

TABLE 1-continued

3-ARYL-4(α-(1 H-IMIDAZOL-1-YL) BENZYL-1H-PYRROLES-1-SUBSTITUTED

| Abbreviation | X | R | X' |
|---|---|---|---|
| RDS 155 | CH3 | Ⓐ | H |

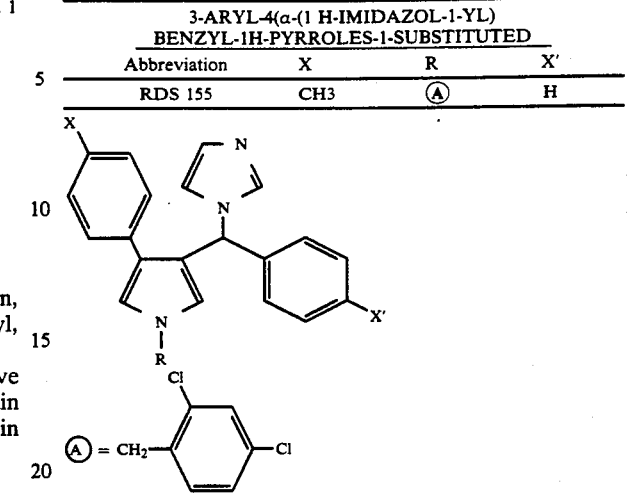

Ⓐ = CH2— (2,4-dichlorophenyl)

TABLE 2

Chemical and physical properties

| Compound | Formula | M.W. | m.p. °C. | Crystallized from | Yield % | Analysis C % | H % | Calcium found | Cl % | F % |
|---|---|---|---|---|---|---|---|---|---|---|
| RDS 105 | C20H17N3 | 299.36 | 170-1 | benzene | 94.2 | 80.24 | 5.72 | 14.04 | | |
| | | | | | | 80.22 | 5.88 | 13.95 | | |
| RDS 124 | C21H19N3 | 313.39 | 110-1 | benzene-cyclohexane | 56.3 | 80.48 | 6.11 | 13.41 | | |
| | | | | | | 80.43 | 6.06 | 13.29 | | |
| RDS 120 | C27H21Cl2N3 | 458.38 | 51-2 | benzene-cyclohexane | 49.0 | 70.74 | 4.62 | 9.17 | 15.47 | |
| | | | | | | 70.61 | 4.70 | 9.04 | 15.62 | |
| RDS 126 | C20H16ClN3 | 297.31 | 218-9 | ethanol | 71.4 | 71.96 | 4.83 | 12.59 | 10.62 | |
| | | | | | | 71.89 | 4.77 | 12.39 | 10.66 | |
| RDS 133* | C27H21Cl3N4O3 | 555.84 | 145-6 | ethanol-ethyl ether | 62.7 | 58.34 | 4.52 | 10.08 | 19.14 | |
| | | | | | | 58.30 | 4.53 | 10.05 | 19.13 | |
| RDS 128 | C20H16FN3 | 317.35 | 195-6 | ethanol | 46.9 | 75.69 | 5.08 | 13.24 | | 5.99 |
| | | | | | | 75.51 | 5.18 | 12.99 | | 6.02 |
| RDS 134 | C21H18FN3 | 331.38 | 83-5 | benzene | 88.4 | 76.11 | 5.48 | 12.68 | | 5.73 |
| | | | | | | 76.00 | 5.53 | 12.71 | | 5.73 |
| RDS 132* | C27H21Cl2FN4O3 | 539.38 | 143-4 | isopropanol | 86.4 | 60.12 | 3.92 | 10.39 | 13.15 | 3.52 |
| | | | | | | 60.20 | 4.00 | 10.25 | 13.10 | 3.60 |
| RDS 138 | C21H19N3O | 329.39 | 175-8 | benzene | 48.9 | 76.57 | 5.81 | 12.76 | | |
| | | | | | | 76.56 | 6.00 | 12.48 | | |
| RDS 139 | C22H21N3O | 343.41 | 87-9 | benzene-cyclohexane | 01.4 | 76.94 | 6.16 | 12.24 | | |
| | | | | | | 76.72 | 6.33 | 12.17 | | |
| RDS 141* | C28H24Cl2N4O4 | 551.42 | 123-5 | ethanol-ethyl ether | 77.3 | 60.99 | 4.52 | 10.16 | 12.86 | |
| | | | | | | 60.71 | 4.53 | 10.38 | 12.86 | |
| RDS 143 | C21H19N3 | 313.39 | 153-4 | toluene | 49.8 | 80.48 | 6.11 | 13.41 | | |
| | | | | | | 80.40 | 6.20 | 13.42 | | |
| RDS 158 | C22H21N3 | 327.41 | 130-1 | benzene-cyclohexane | 76.7 | 80.70 | 6.47 | 12.48 | | |
| | | | | | | 80.48 | 6.69 | 12.76 | | |
| RDS 155* | C28H24Cl2N4O3 | 535.42 | 165-8 | isopropanol | 73.9 | 62.81 | 4.52 | 13.25 | 13.25 | |
| | | | | | | 62.75 | 4.53 | 13.24 | 13.24 | |

*As nitrates

Another purpose of the present invention is that of providing a process for the preparation of the compounds of the present invention and as above defined, this process being characterized by the following steps:

(a) reaction between 3-(4-phenyl substituted)-1-phenyl-2-propen-1-one and tosylmethylisocianide in an organic solvent or a mixture of organic solvents, preferably mixtures of dimethylsulfoxide and ethyl ether, at room temperature;

(b) methylation in an organic solvent of the resulting 4-benzoyl-3-(4'-phenylsubstituted)-1-methyl-1H-pyrrole, with a methylating agent, at high temperature of between 80° C. and 150° C., leading to benzoyl-3-(4'-phenylsubstituted)-1-methyl-1H-pyrrole, the solvent being preferably dimethylformamide;

(c) reduction of the obtained compound with an alkaline hydride in an organic solvent giving 3-(4-phenyl-substituted)-4-[(1-hydroxy)-benzyl]-1-methyl-1H-pyrrole, the organic solvent being preferably anhydrous tetrahydrofuran, and (d) reaction of the obtained compound with 1,1'-carbonyldiimidazole in an organic solvent, preferably acetonitrile, at room temperature, and recovery of the desired final compound.

It is worth to notice that, as it will be appreciated from the above definitions and from the following examples, the solvents used in the several steps are specific, since the reactants are compounds difficultly soluble in the normal solvents. In the following scheme the process of the present invention is illustrated with reference to the compound identified in the tables 1 and 2 with the abbreviation RDS 125, the following example detailedly explaining the preparation of this compound.

Of course this example has no limiting but only illustrating meaning.

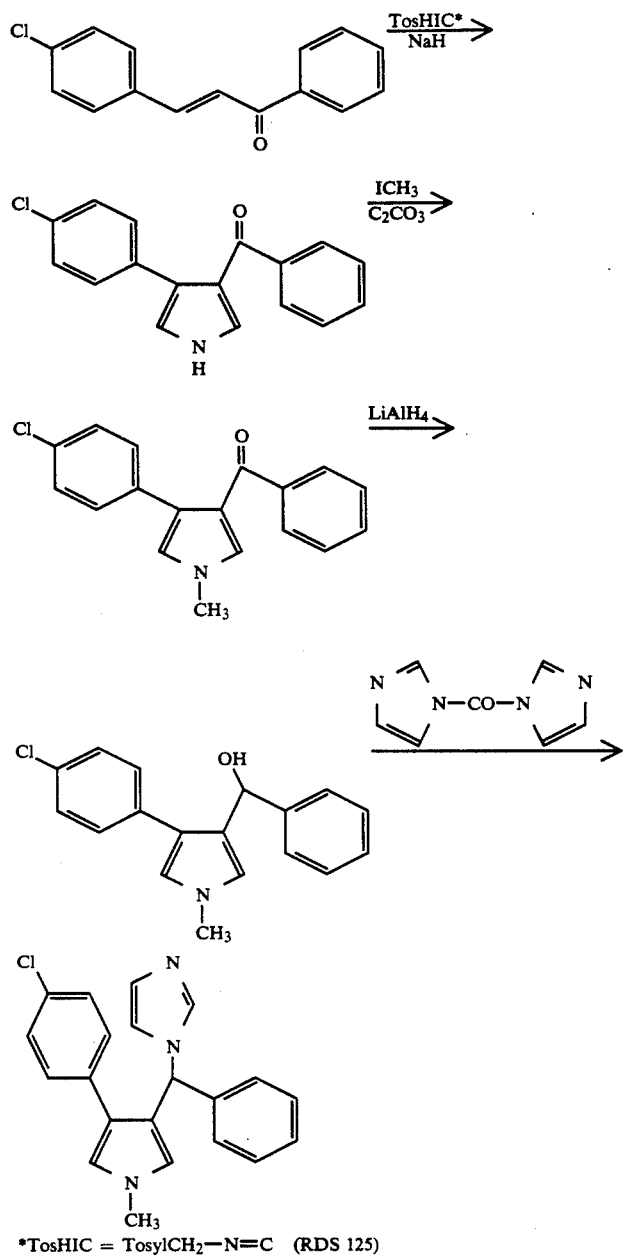

*TosHIC = TosylCH₂—N=C   (RDS 125)

EXAMPLE 1

Preparation of 3-(4'-chlorophenyl)-4-[α-(1-imidazol-1-yl)benzyl]-1-methyl-1H-pyrrole (RDS 125)

(a) Synthesis of 4-benzoyl-3-(-4-chlorophenyl)-1H-pyrrole,

A suspension of NaH (80% in paraffin) (3.97 g; 0.165 moles) in anhydrous ethyl ether (100 ml), maintained under nitrogen stream, is dropwise added with a solution of 3-(4-chlorophenyl)-1-phenyl-2-propen-1-one (18.11 g; 0075 moles) and tosylmethylisocianide (TOSMIC) (14.60 g; 0.075 moles) in anhydrous dimethylsulfoxide (170 ml) diluted with anhydrous ethyl ether (300 ml). Upon the additions are completed, the mixture is maintained under stirring at room temperature for 3 hours. After dilution with water (800 ml) the precipitate is filtered, washed with absolute ethanol and lastly with petroleum ether. There are obtained 10.40 g (yield 49.4%) of 4-benzoyl-3-(4-chlorophenyl)-1H-pyrrole, which is crystallized from N,N-dimethylformamide and water (m.p.: 232°–235° C.).

Chemical characteristics of this first intermediate compound:

IR (nujol): 3140 (NH), 1605 cm$^{-1}$(CO).

$^1$H-NMR (DMF-d7): 7.23–7.70 (m, 9H, pyrrole protons and 7 benzene protons), 7.80 and 8.00 (m, 2H, 2 benzene protons), 11.82 ppm (broad s, 1H, NH).

Elemental analysis for $C_{17}H_{12}ClNO$: calculated: C=72.47; H=4.29; N=4.97; Cl=12.59 found: C=72.61; H=4.30; N=5.07; Cl=12.43

(b) Synthesis of 4-benzoyl-3-(4-chlorophenyl)-1-methyl-1H-pyrrole,

A suspension of 4-benzoyl-3-(4-chlorophenyl)-1H-pyrrole (3.50 g; 0.0012 moles) in anhydrous dimethylformamide (20 ml) is supplemented with methyl iodide (12.66 g; 0.089 moles) and anhydrous potassium carbonate (3.43 g; 0.025 moles). The mixture is maintained under stirring at 90° C. for 16 hours, then poured on water (200 ml) and extracted with ethyl acetate (3×100 ml). The combined organic extracts, after washing with a saturated solution of sodium chloride (3×200 ml), are dried on anhydrous sodium sulfate and the solvent is removed under reduced pressure. The residue is chromatographed on alumina by eluting with chloroform leading to 3.39 g (yield 92.4%) of benzoyl-3-(4'-chlorophenyl)-1-methyl-1H-pyrrole.

Chemical characteristics of the second intermediated compound:

m.p. 126°–129° C. from benzene/cyclohexane.

IR (nujol): 1630 cm$^{-1}$(CO)

$^1$H-NMR (CDCl3: 3.65(s, 3H, CH3), 6.72 (d, J=2.2 Hz, 1H, pyrrole proton), 7.03 (d, J=2.2 Hz, 1H, pyrrole proton) 7.16–7.57 (m, 1H,benzene protons), 7.73–7.93 ppm (m, 2H, benzene protons).

Elemental analysis for $C_{18}H_{14}ClNO$: calculated: C=73.09; H=4.77; N=4.74; Cl=11.99; found: C=73.30; H=4.78; N=4.87; Cl=11.90.

(c) Sinthesis of 3-(4-chlorophenyl)-4-[−(1-hydroxy)-benzyl]- -1-methyl-1H-pyrrole A solution of 4-benzoyl-3-(4-chlorophenyl)-1-methyl-1H-pyrrole (2.89 g; 0.010 moles) in anhydrous tetrahydrofuran (70 ml) is cautiously added to a suspension of lithium and aluminum hydride (0.53 g; 0.014 moles) in 70 ml of anhydrous tetrahydrofuran cooled to 0° C. The mixture is maintained under stirring at room temperature for 1.5 hours, the excess hydride is removed with ground ice, and the solution is filtered and concentrated to small volume. The residue is taken with chloroform and the organic solution is washed with a saturated solution of sodium chloride. By drying on anhydrous sodium sulfate and subsequent removal of the solvent under reduced pressure there are obtained 2.89 g (yield 100%) of 3-(4-chlorophenyl)-4-[α- -(1-hydroxy)-benzyl]-1-methyl-1H-pyrrole.

Chemical characteristics of the third intermediate compound.

m.p.: 108°–109° C. from cyclohexane.

IR (nujol): 3270 cm$^{-1}$(OH).

$^1$H-NMR (CDCl3): 2.12 (broad s, 1H, OH), 3.53 (s, 3H, CH3), 5.82 (s, 1H, CH), 6.25 and 6.70 (2d, J=2.2 Hz, 2H pyrrole protons), 6.90–7.65 (m, 9H, benzene protons).

Elemental analysis for $C_{18}H_{16}ClNO$ calculated: C=72.60; H=5.42; N=4.70; Cl=11.91 found: C=72.80; H=5.24; N=4.45; Cl=11.98.

(d) Synthesis of 3-(4-chlorophenyl)-4-[α-(1-imidazol-1-yl)benzyl]- -1-methyl-1H-pyrrole.

A solution of 3-(4-chlorophenyl)-4-[α-(1-hydroxy)-benzyl]- -1-methyl-1H-pyrrole (2.29 g; 0.008 moles) in anhydrous acetonitrile (130 ml) and 1,1'-carbonyldiimidazole (2.50 g; 0.015 moles) is maintained under stirring for 16 hours at room temperature. Further 1,1'-carbonyldiimidazole (2.50 g) is added and the mixture is maintained under stirring at room temperature for further 3 hours. After removal of the solvent at room temperature, the residue is taken with ethyl acetate (200 ml), washed with a saturated solution of sodium chloride (3×100 ml) and dried on sodium sulfate. Upon evaporation of the solvent at reduced pressure there are obtained 2.78 g (yield 100%) of 3-(4-chlorophenyl)-4-[α-(1-imidazol-1-yl)benzyl]-1- -methyl-1H-pyrrole.

Chemical characteristics of the final product.

m.p.: 157°–159° C. from benzene.

1H-NMR (CDCl3): δ3.58 (s, 3H, CH3), 6.15 (d, J=2.2 Hz, 1H, pyrrole proton), 6.37 (d, J=2.2 Hz, 1H, pyrrole proton), 6.88–7.45 (m, 11H, 9 benzene protons and 2 imidazole protons), 7.50 (m, 1H, imidazole proton).

Elemental analysis for $C_{21}H_{18}ClN_3$ calculated: C=72.51; H=5.22; N=12.08; Cl=10.19 found: C=72.33; H=5.44; N=11.90; Cl=10.08.

With a like process, apart from suitable variations depending on the differences of the substituents X, X' and R, the other compounds have been obtained, the characteristics of which are reported in the tables 1 and 2. Pharmacological and toxicological tests have been carried out on several compounds of the present invention.

ANTIMICROBIAL ACTIVITY

For the tests of antimicrobial activity each compound being tested and two reference antifungine substances (econazole nitrate, miconazole nitrate) have been dissolved in dimethylsulfoxide (DMSO) at the concentration of 5 mg/ml and then brought to the desired concentrations in the culture mediums. For the tests with the mycetes the following mediums have been used:

a) Sabouraud medium (pH=5.6, BBL). In some tests it has been supplemented with serum at variable concentrations (0.2%, 0.5%, 1%, 5%). In some experiments Sabouraud medium has been used at pH of between 4.5 and 7.0: the medium has been brought to the desired pH by means of 0.1N HCl or 0.1N NaOH.

b) Eagle's Minimum Essential Medium (MEM) (pH=5.6).

c) Yeast Nitrogen Base (YNB) (Difco, pH=6.0).

For the tests with Gram positive bacteria the Mueller-Hinton medium (BBL) has been used (pH=7.2).

The 80 strains of Candica albicans used for the tests originated partially from biological material and partly from collection strains. The inoculum (33 μl) was obtained from cultures grown in Sabouraud medium for 18 hours at 37° C.; from the initial concentration of 20×16 cells/ml (controlled by means of a Carl Zeiss OD540 spectrophotometer) the cultures were diluted in physiological solution and brought to the final concentration of 3×10 cells/ml.

In the tests carried out with 20 strains of Streptococcus faecalis freshly isolated from biological material, the inoculum (33 μl) was obtained from cultures grown in Mueller-Hinton medium for 18 hours at 37° C. and then diluted in physiological solution and adjusted to the final concentration of $10^4$ cells/ml. The experiments were effected in microtiters in which 0.2 ml of medium containing scalar dilutions of antifungine agent were injected.

The inoculum (33 μ) contained $3 \times 10^3$ cells/ml. The minimum inhibiting concentration (MIC) was determined after incubation of 48 hours at 37° C. The tests for the mycetes were effected in Sabouraud medium, in YNB, MEM and, for the bacteria, in MH. Besides MIC also the minimum cytocide action (MBC) has been assessed, controlled on subcultures seeded in liquid medium without antimycotic compound and examined after 48 hours of incubation at 37° C. The results of the microbiological tests are reported in the tables 3 and 4.

TABLE 3

MINIMUM INHYBITING CONCENTRATIONS OF PYRROLIC ANTIMYCOTIC COMPOUNDS ON DIFFERENT TYPES OF FUNGI

| Compound | CA | MC | MG | TR | TM | EF |
|---|---|---|---|---|---|---|
| Miconazole | 3.12 | 0.12 | 0.89 | 0.78 | 4.29 | 0.19 |
| Econazole | 3.09 | 0.25 | 0.78 | 0.39 | 3.78 | 0.09 |
| RDS 105 | >6.00 | 2.45 | 2.00 | 1.89 | >6.00 | >6.00 |
| RDS 124 | 4.68 | 1.67 | 2.78 | 1.23 | >6.00 | 1.20 |
| RDS 120 | >6.00 | >6.00 | >6.00 | >6.00 | >6.00 | >6.00 |
| RDS 126 | 1.89 | 0.13 | 0.78 | 0.45 | 3.56 | 0.11 |
| RDS 125 | 1.03 | 0.08 | 0.14 | 0.11 | 1.34 | 0.03 |
| RDS 133 | 1.78 | 0.11 | 0.56 | 0.61 | 2.66 | 0.10 |
| RDS 128 | 1.45 | 0.09 | 0.34 | 0.18 | 2.51 | 0.13 |
| RDS 134 | 2.21 | 0.16 | 0.29 | 0.31 | 2.80 | 0.10 |
| RDS 132 | 4.56 | 0.26 | 1.23 | 1.14 | 5.89 | 0.23 |
| RDS 138 | >6.00 | 2.34 | 1.78 | 1.30 | >6.00 | 2.07 |
| RDS 139 | 2.11 | 1.12 | 2.20 | 1.05 | >6.00 | 0.89 |
| RDS 141 | >6.00 | >6.00 | >6.00 | >6.00 | >6.00 | >6.00 |
| RDS 143 | 1.56 | 0.23 | 0.81 | 0.67 | 3.45 | 0.23 |
| RDS 158 | 1.05 | 0.09 | 0.18 | 0.13 | 1.41 | 0.04 |
| RDS 155 | 2.45 | 0.24 | 1.01 | 0.56 | 2.56 | 0.18 |

Legend:
CA = Candida albicans;
MC = Microsporum canis;
MG = Microsporum gypseum;
TR = Trichophylon rubrum;
TM = Trichophylon mentagrophytes;
EF = Epidermophylon floccusum.

TABLE 4

MINIMUM INHYBITING CONCENTRATIONS (UG/ML) OF PYRROLIC ANTIMYCOTIC COMPOUNDS ON DIFFERENT TYPES OF BACTERIA

| Compound | St. faecalis | St. aureus |
|---|---|---|
| Miconazole | 12.75 | 11.89 |
| Econazole | 6.67 | 6.89 |
| RDS 105 | >12.00 | >12.00 |
| RDS 124 | >12.00 | >12.00 |
| RDS 120 | >12.00 | >12.00 |
| RDS 126 | 5.67 | 4.66 |
| RDS 125 | 3.23 | 2.77 |
| RDS 133 | 4.50 | 3.77 |
| RDS 128 | 5.20 | 5.00 |
| RDS 134 | 4.55 | 4.89 |
| RDS 132 | 6.11 | 5.67 |
| RDS 138 | >12.00 | >12.00 |
| RDS 139 | >12.00 | >12.00 |
| RDS 141 | >12.00 | >12.00 |
| RDS 143 | 4.78 | 5.01 |
| RDS 168 | 3.89 | 4.12 |
| RDS 155 | 5.29 | 4.78 |

The pyrrole derivatives according to the present invention are to be used as the active ingredients for pharmaceutical compositions useful in the treatment of diseases induced from mycetes and pathogenic bacteria.

The pharmaceutical compositions are in form suitable both for topical application, as creams, pommades, lotions, gels, ointments, powders, liquid solutions, capsules, ovules and other forms useful for vaginal use, and for systemic administration, the latter meaning both forms for oral assumption (such as tablets, capsules, granulates and the like) and forms for parenteral administration. These forms are rendered possible by the fact that the compounds of the invention are soluble.

For the preparation of the pharmaceutical compositions according to the invention the standard pharmaceutical techniques are used, together with the conventional vehicles and excipients.

As regards the unit dosages of the pharmaceutical compositions, they normally vary in a range of 0.5-2% for topical administration and depending on the type of disease to be treated.

I claim:

1. A pyrrole compound of the formula:

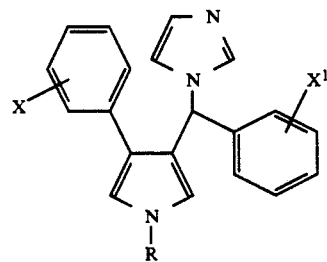

wherein each of X and X' is selected from the group consisting of H, lower alkyl, lower alkoxy, halogen, nitro, and amino, and R is selected from the group consisting of H, lower alkyl, phenyl, phenyl-lower alkyl, and cyclo-loweralkylmethyl.

2. A pyrrole compound according to claim 1, which is 3-(4-chlorophenyl)-4-[α-(1-imidazol-1-yl)benzyl]-1-methyl-1-H-pyrrole.

3. A pyrrole compound according to claim 1, which is 3-(4-methylphenyl)-4-[α(1-imidazol-1-yl)benzyl]-1-methyl-1-H-pyrrole.

4. A pyrrole compound according to claim 1, wherein X is chlorine, R is H and X' is H.

5. A pyrrole compound according to claim 1, selected from the group consisting of:
   (1) wherein X is H, R is H and X' is H;
   (2) wherein X is H, R is CH₃ and X' is H;
   (3) wherein X is H, R is 2,4-dichlorobenzyl and X' is H;
   (4) wherein X is Cl, R is H and X' is H;
   (5) wherein X is Cl, R is CH₃ and X' is H;
   (6) wherein X is Cl, R is 2,4-dichlorobenzyl and X' is H;
   (7) wherein X is F, R is H and X' is H;
   (8) wherein X is F, R is CH₃ and X' is H;
   (9) wherein X is F, R is 2,4-dichlorobenzyl and X' is H;
   (10) wherein X is methoxy, R is H and X' is H;
   (11) wherein X is methoxy, R is methyl and X' is H;
   (12) wherein X is methoxy, R is 2,4-dichlorobenzyl and X' is H;
   (13) wherein X is methyl, R is H and X' is H;
   (14) wherein X is methyl, R is methyl and X' is H and
   (15) wherein X is methyl, R is 2,4-dichlorobenzyl and X' is H.

6. A pharmaceutical composition suitable for systemic or topical application in the treatment of diseases induced from pathogenic mycetes and bacteria, comprising as active ingredient, an effective amount of a pyrrole compound according to claim 1 together with an inert vehicle or excipient.

7. A pharmaceutical composition according to claim 6, wherein said pyrrole compound is 3-(4-chlorophenyl)-4-[α-(1-imidazol-1-yl)benzyl]-1-methyl-1-H-pyrrole.

8. A pharmaceutical composition according to claim 6, wherein said pyrrole compound is 3-(4-methylphenyl)-4-[α(1-imidazol-1-yl)benzyl]-1-methyl-1-H-pyrrole.

* * * * *